(12) United States Patent
Roger

(10) Patent No.: US 7,618,406 B2
(45) Date of Patent: Nov. 17, 2009

(54) BREAK SEAL BEFORE ACCESS DUAL CHAMBER BAG

(75) Inventor: Rodolfo Roger, Clearwater, FL (US)

(73) Assignees: Baxter International, Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 11/625,683

(22) Filed: Jan. 22, 2007

(65) Prior Publication Data

US 2008/0177243 A1    Jul. 24, 2008

(51) Int. Cl.
*A61B 19/00* (2006.01)

(52) U.S. Cl. ............... 604/410; 604/408; 604/409; 604/411; 206/219; 206/484; 383/107; 383/109

(58) Field of Classification Search ......... 604/408–411; 220/501, 62.22; 383/210.1
See application file for complete search history.

(56) References Cited

U.S. PATENT DOCUMENTS

| | | | |
|---|---|---|---|
| 3,085,681 A | | 4/1963 | Fazzari |
| 3,093,507 A | * | 6/1963 | Lander et al. ............... 438/787 |
| 4,658,433 A | * | 4/1987 | Savicki ........................ 383/63 |
| 5,371,221 A | * | 12/1994 | Sipos et al. ................. 544/275 |
| 5,380,315 A | | 1/1995 | Isono et al. |
| 5,431,496 A | | 7/1995 | Balteau et al. |
| 5,462,526 A | * | 10/1995 | Barney et al. ................. 604/85 |
| 5,560,403 A | | 10/1996 | Balteau et al. |
| 5,580,349 A | * | 12/1996 | Thor et al. ................... 604/406 |
| 5,728,087 A | * | 3/1998 | Niedospial, Jr. ............. 604/408 |
| 5,896,989 A | * | 4/1999 | Ropiak et al. ................ 206/438 |
| 5,944,709 A | * | 8/1999 | Barney et al. ............... 604/410 |
| 6,024,220 A | * | 2/2000 | Smith et al. .................. 206/484 |
| 6,039,720 A | | 3/2000 | Wieslander |
| 6,267,564 B1 | * | 7/2001 | Rapheal ...................... 417/234 |
| 6,319,243 B1 | | 11/2001 | Becker et al. |
| 6,764,567 B2 | | 7/2004 | Sperko et al. |
| 6,846,305 B2 | | 1/2005 | Smith et al. |
| 6,968,952 B2 | | 11/2005 | Crevier et al. |
| 6,996,951 B2 | | 2/2006 | Smith et al. |
| 7,169,138 B2 | | 1/2007 | Becker et al. |
| 2005/0194060 A1 | | 9/2005 | Houwaert et al. |
| 2006/0093765 A1 | | 5/2006 | Mueller |
| 2007/0029001 A1 | | 2/2007 | Trouilly et al. |
| 2007/0092579 A1 | | 4/2007 | Trouilly et al. |

FOREIGN PATENT DOCUMENTS

| | | |
|---|---|---|
| EP | 1 693 043 A1 | 8/2006 |
| WO | 99/20222 A1 | 4/1999 |
| WO | PCT/US2007/085701 | 6/2008 |

* cited by examiner

*Primary Examiner*—Ilya Y Treyger
(74) *Attorney, Agent, or Firm*—K&L Gates LLP

(57) ABSTRACT

A multiple chamber medical fluid bag including: (i) a flexible enclosure; (ii) a first fluid chamber formed in the enclosure; (iii) a second fluid chamber formed in the enclosure; (iv) the first fluid chamber and the second fluid chamber separated by a frangible seal; and (v) an access port connected to the enclosure, the enclosure folded so as to cover the access port and so that the frangible seal is broken to uncover the access port.

10 Claims, 15 Drawing Sheets

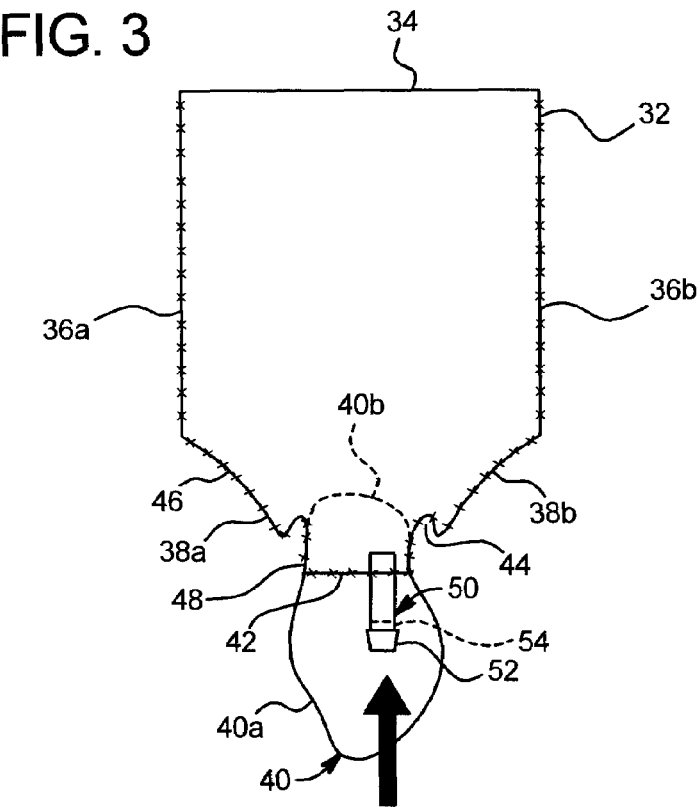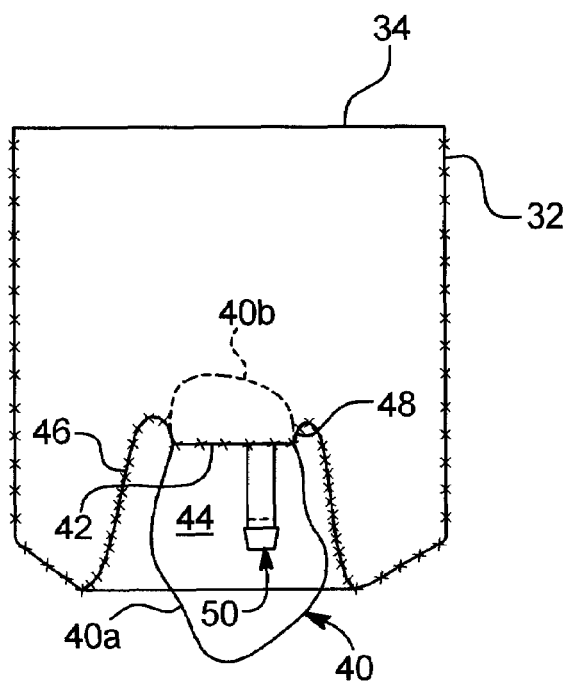

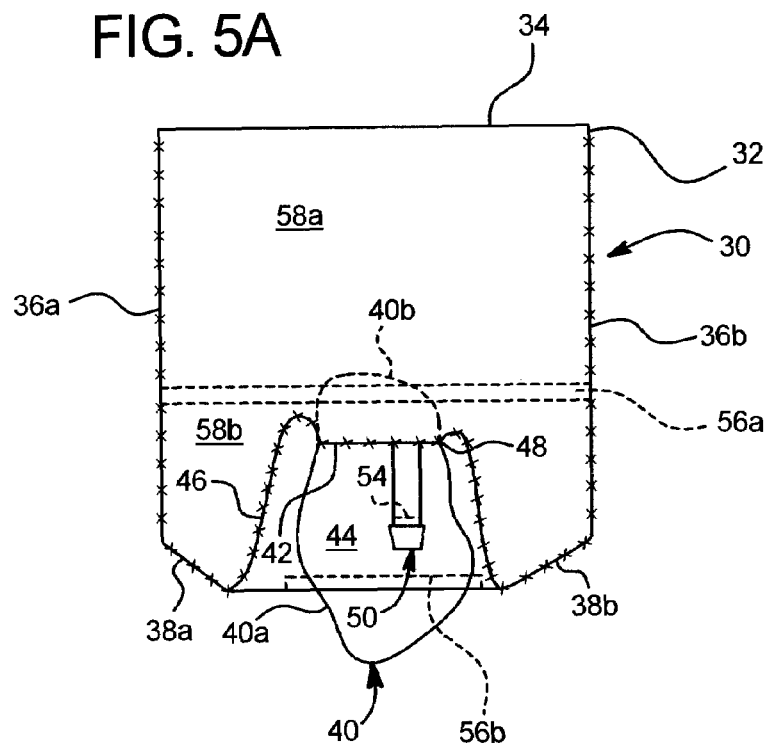
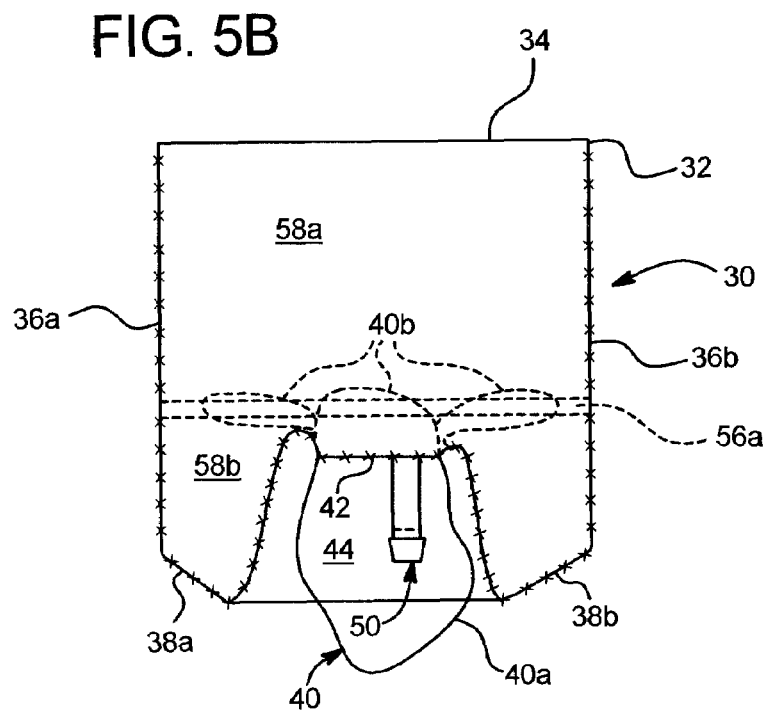

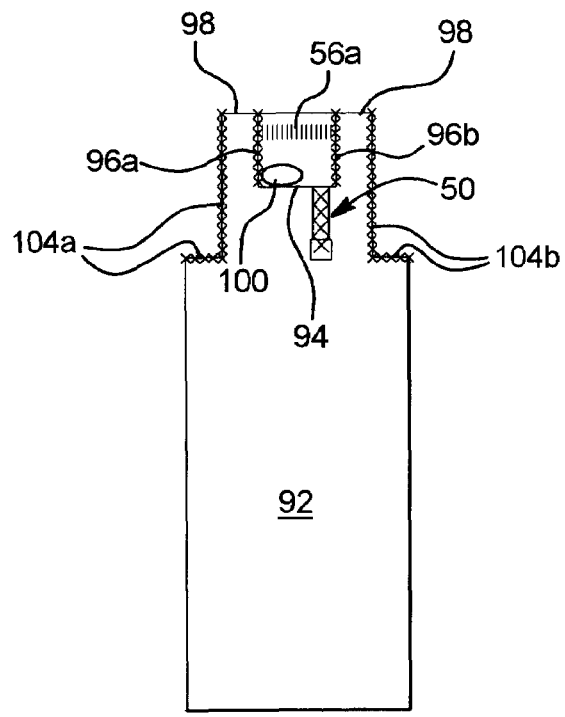
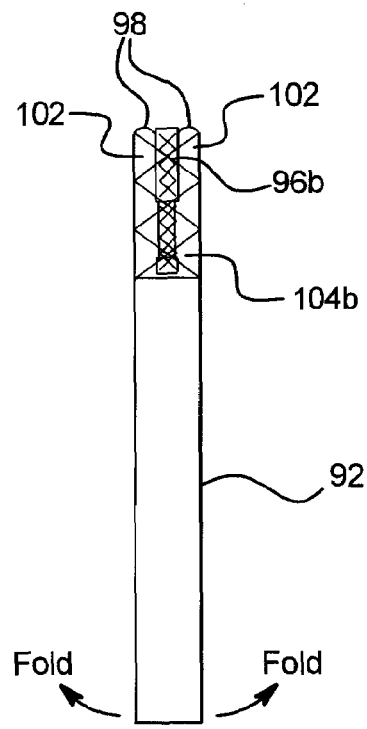
FIG. 16A   FIG. 16B
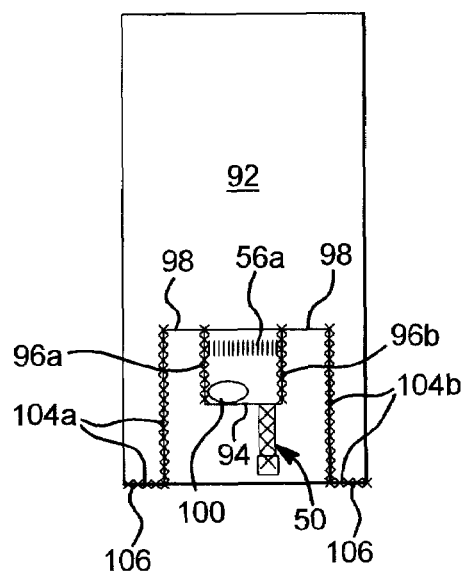
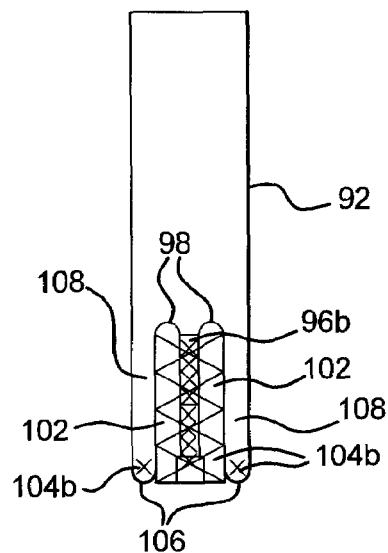
FIG. 17A   FIG. 17B

BREAK SEAL BEFORE ACCESS DUAL CHAMBER BAG

BACKGROUND

The present disclosure relates to medical fluid solution bags and more particularly to dual chamber solution bags.

Various medical treatments, such as peritoneal dialysis, use dual bag solutions. Peritoneal dialysis solution is called dialysate. Dialysate has traditionally included lactate in a single chamber bag. More recently, dialysate has been made to be bicarbonate based. Bicarbonate is unstable in the presence of magnesium and calcium and forms a precipitate after a period of time. Accordingly, bicarbonate based dialysate needs to be packaged in a dual chamber supply bag.

The two chambers of the dual chamber bag are separated by a seal that a person breaks without tearing the entire bag. One such seal provided by the assignee of the present disclosure is termed a peel seal. Prior to use, the patient or caregiver breaks the seal between the two chambers and the solution from the two chambers is mixed and used before a calcium or magnesium precipitate can form.

The two unmixed solutions separated by the peel seal pose a risk. Each solution taken individually is physiologically unsafe for the patient. Accordingly, it is necessary to properly mix the individual solutions to form the final solution before injecting any of the solutions into the patient or contacting any of the solutions with the patient's blood.

FIG. 1 illustrates a known dual chamber bag 10. A medical fluid system, such as a peritoneal dialysis system, is connected to bag 10 via an access system 20. Access system 20 is connected fluidly to chamber 12. When it is desired to use the combined solution within bag 10, a frangible seal 14 is broken allowing solution A residing within chamber 16 to mix with solution B residing within chamber 12.

As alluded to above, bag 10 presents an inherent risk. If after connecting the bag 10 to the patient, the seal between chamber 12 and access system 20 is broken before frangible seal 14 is broken (allowing solutions A and B to mix), a potentially physiologically unsafe solution B is allowed to reach the patient or to contact the patient's blood.

Accordingly, an improved dual chamber solution bag is needed.

SUMMARY

The dual chamber bags described herein can be used for different medical fluid therapies. In one embodiment, the dual chamber bag is a peritoneal dialysate bag. In another embodiment, the dual chamber bag stores dialysate used for hemodialysis, such as home hemodialysis. Here, the interest in home hemodialysis is increasing. Patients would typically rather have hemodialysis performed at home than in a center. In certain areas of the country, hemodialysis centers are located remotely, requiring a long drive or other transport on top of the time needed for the therapy itself. Further, performing treatment while the patient is relaxing or even sleeping lessens the interruption of the patient's active day. Bagged dialysate is also used for in-center hemodialysis treatments. The dual chamber bags described herein are also useful for substitution or replacement fluids, for example, for hemofiltration or hemodiafiltration, wherein it is again desirable to keep multiple solutions separate prior to use.

Described herein are dual chamber bags and processes for making the same, wherein in general, the frangible or peel seal needs to be broken before or in order to make a connection between the patient and the access system of the bag.

Illustrated below are multiple embodiments for embedding the access system or access port within the bag. For example, the access port or access system can be embedded entirely within one or both of the chambers.

In each embodiment, a handle is provided that allows the user to pull the access system from within the dual chamber bag to make it available to be connected to a patient. The handle and the access port are connected to an intermediate or force transfer device that is in turn connected or part of the frangible or peel seal. For example, the intermediate device can be a cord, string, ribbon, monofilament or sheet of plastic. The plastic or film for example can be the same as that used to make the dual chamber bag. The intermediate or force transfer device is configured to withstand a force larger than that needed to break the frangible seal. The intermediate device is also configured to be part of or integrated with the peel seal. That is, it is formed with the seal used to separate the dual chambers from each other.

As seen herein, the dual chamber bags can have one or a plurality of frangible seals. The seals can be located perpendicular to or parallel to a direction of the access port. For example one seal can be used to separate the two chambers, while a second seal separates the access system from the rest of the bag.

As seen below, the access port is buried within the bag, isolating it from the patient until the main seal is broken. The bag in certain embodiments is folded multiple times to achieve a desired configuration relative to the access system. During the folding process, the force transfer or intermediate device linking the handle with the seal is applied, e.g., welded, to the bag.

As further seen below, one or more sides or seams of the bags are welded, e.g., sonically, via heat seal and/or chemically welded. The folds and the welds result in a dual chamber bag that partially or completely embeds the access system until the main peel seal separating the two chambers is broken.

It is therefore an advantage of the present disclosure to provide a dual chamber medical fluid bag having increased safety.

It is another advantage of the present disclosure to provide a dual chamber bag in which a frangible seal separating first and second individual solutions needs to be broken before an access system allowing access to the dual chamber bag can be reached and connected to the patient.

It is a further advantage of the present disclosure to provide a dual chamber bag that is relatively easy to form.

It is another advantage of the present disclosure to provide a dual chamber bag that is made of relatively inexpensive components.

Additional features and advantages are described herein, and will be apparent from, the following Detailed Description and the figures.

BRIEF DESCRIPTION OF THE FIGURES

FIGS. 2 to 5A are elevation views illustrating one dual chamber bag and method of making same according to the present disclosure.

FIG. 5B is an alternative dual chamber bag to the one shown in connection with FIG. 5A.

FIGS. 11A to 11C, 12A, 12B, 13A, 13B, 14A, 14B, 15A, 15B, 16A, 16B, 17A, 17B, 18A, 18B, 19A, 19B and 20A to 20B illustrate a further alternative dual chamber bag and method of making same according to the present disclosure.

DETAILED DESCRIPTION

Figure 1:
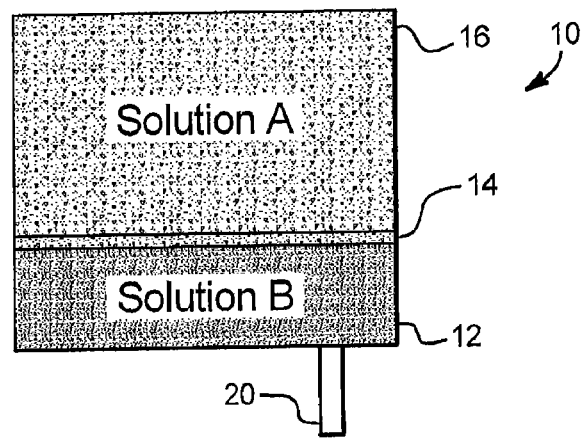
FIG. 1 is an elevation view of a prior art dual chamber bag.
Figure 2:
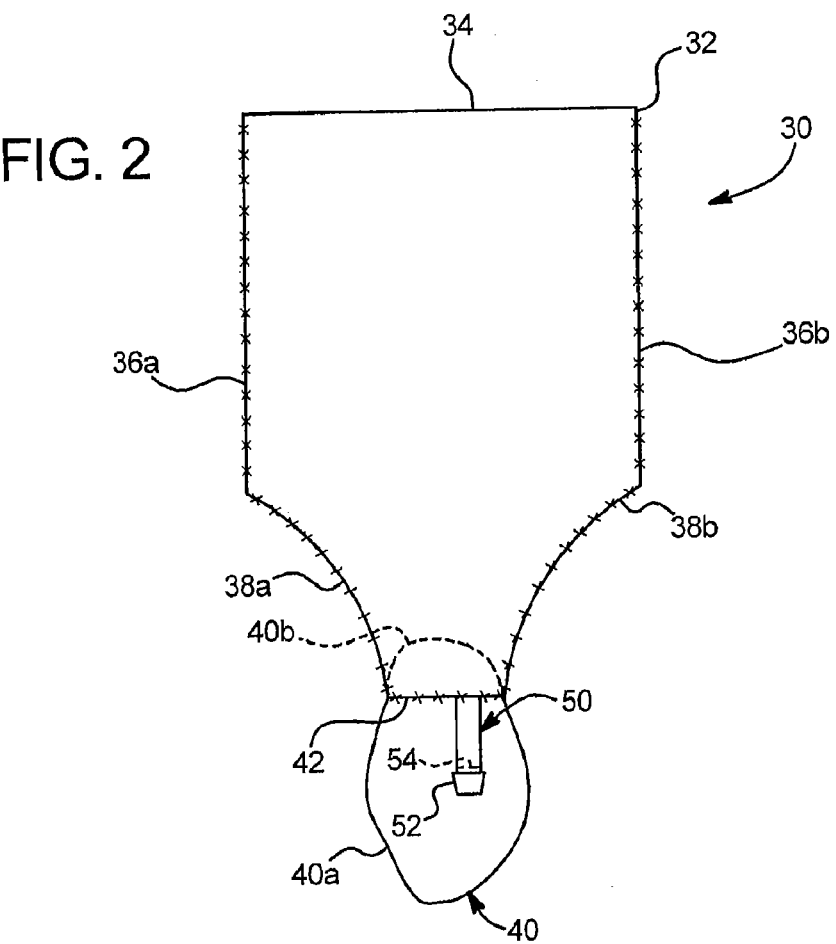

Referring now to FIGS. 2 to 5A, a first embodiment for and method of making a dual chamber bag according to the present disclosure is illustrated by bag 30 (completed in FIG. 5A). FIG. 2 illustrates a first manufacturing figure for dual chamber bag 30. Here, an overall enclosure 32 is formed by folding a piece of material for enclosure 32 along fold line 34. The material for enclosure 32 and indeed for each of the enclosures discussed herein is any one or more of polyvinyl chloride ("PVC"), Japanese polyolefinic container ("JPOC"), propylene/ethylene copolymer ("cPP"), polypropylene ("PP"), polyamide ("PA") and combinations thereof. Sides 36a and 36b and 38a and 38b are welded together as shown via the X's or weld marks. Suitable processes for forming weld seams 36a, 36b, 38a, 38b and indeed each of the welded seams discussed herein include chemical bonding, heat sealing, ultrasonic sealing, radio frequency sealing, microwave sealing and combinations thereof.

As seen, a string or pull handle 40 is welded into a portion of seams 38a and 38b, such that a first portion 40a of string 40 resides outside of enclosure 32, while a second portion 40b of string 40 is looped inside enclosure 32. Suitable material for string 40 includes any of the materials listed above. Inner portion 40b can be welded to seams 38a and 38b after such seams have been formed. Alternatively, inner portion 40b of string 40 is welded with seams 38a and 38b to form enclosure 32.

An access system 50 is welded to enclosure 32 at welded seam 42, which is located distally from folded seam 34. Access system 50 includes a connector 52 that connects to a line leading to a disposable cassette used with a medical fluid machine, such as a peritoneal dialysis, hemodialysis, hemofiltration or other type or renal failure therapy device. Alternatively, the line is a solution line of a manual peritoneal dialysis therapy or continuous ambulatory peritoneal dialysis ("CAPD") treatment. Access system 50 also includes a seal 54, which blocks solution from existing access system 50 until a connection is made with connector 52.

In FIG. 3, the process for embedding access system 50 within enclosure 32 is begun. Here, distal seam 42 is pushed vertically upwards towards folded seam 34, causing welded seams 38a and 38b to buckle, such that a continuous or annular groove 44 begins to form between an outer portion 46 of seams 38a and 38b and an inner portion 48 of those seams.

FIG. 4 illustrates access system 50 embedded completely within enclosure 32. Access system 50 is now surrounded completely by continuous groove or opening 44 created by pushing distal seam 42 connected to access system 50 towards folded line 34. It should be noted that even though access system 50 is embedded with enclosure 32, access system 50 remains external to the enclosure. Only portion 40b of string 40 is actually inside enclosure 32.

Referring now to FIG. 5A, one embodiment of a completed dual chamber bag according to the principals of the present disclosure is illustrated by bag 30. A peel seal 56a is made to separate enclosure 32 into first fluid chamber 58a and second fluid chamber 58b. One suitable apparatus and method for forming the peel seal or frangible seal 56a is set forth in U.S. Pat. No. 6,319,243, entitled, "Containers and Methods for Storing and Admixing Medical Solutions", assigned to the eventual assignee of the present application, the entire contents of which are incorporated herein expressly by reference and relied upon. Importantly, inner portion 40b of string or handle 40 is embedded within and extends through peel seal 56a. In this way, when the patient or caregiver pulls string or handle 40, inner portion 40b is configured and positioned to tear peel seal 56a and allow a first fluid residing within first fluid chamber 58a to mix with a second fluid residing within a second fluid chamber 58b.

Access system 50 is relatively inaccessible to the patient or caregiver before that person pulls string or handle 40 to tear frangible seal 56a and expose access system 50. It is possible however that if someone labored hard enough, they could locate access system 50 within the folds creating opening 44 and puncture seal 54 before pulling string or handle 40. Accordingly, and optionally, a second frangible seal 56b is provided at the open end of opening 44, which seals that open end until handle 40 is pulled, tearing second frangible seal 56b. Here, second peel seal 56b can be fixed or fastened to handle 40, such that it is carried with handle 40 as exposed section 40a of handle 40 is pulled. As seen in FIG. 5B, second frangible seal 56b does not have to fully close the open end of opening 44 but merely make reaching access system 50 impossible or at least highly improbable and impractical.

Referring now to FIG. 5B, an alternative version of dual chamber bag 30 is illustrated. Dual chamber bag 30 of FIG. 5B is like dual chamber bag 30 of FIGS. 1 to 5A in all respect except that inner portion 40b of handle 40 includes multiple string loops or is otherwise expanded such that when exposed portion 40a of handle or string 40 is pulled, the multiple loops or expanded version of inner portion 40b tears open a larger portion of peel seal 56a, increasing the ability of first and second fluids located within first and second chambers 58a and 58b to mix properly and efficiently.

Figure 6:
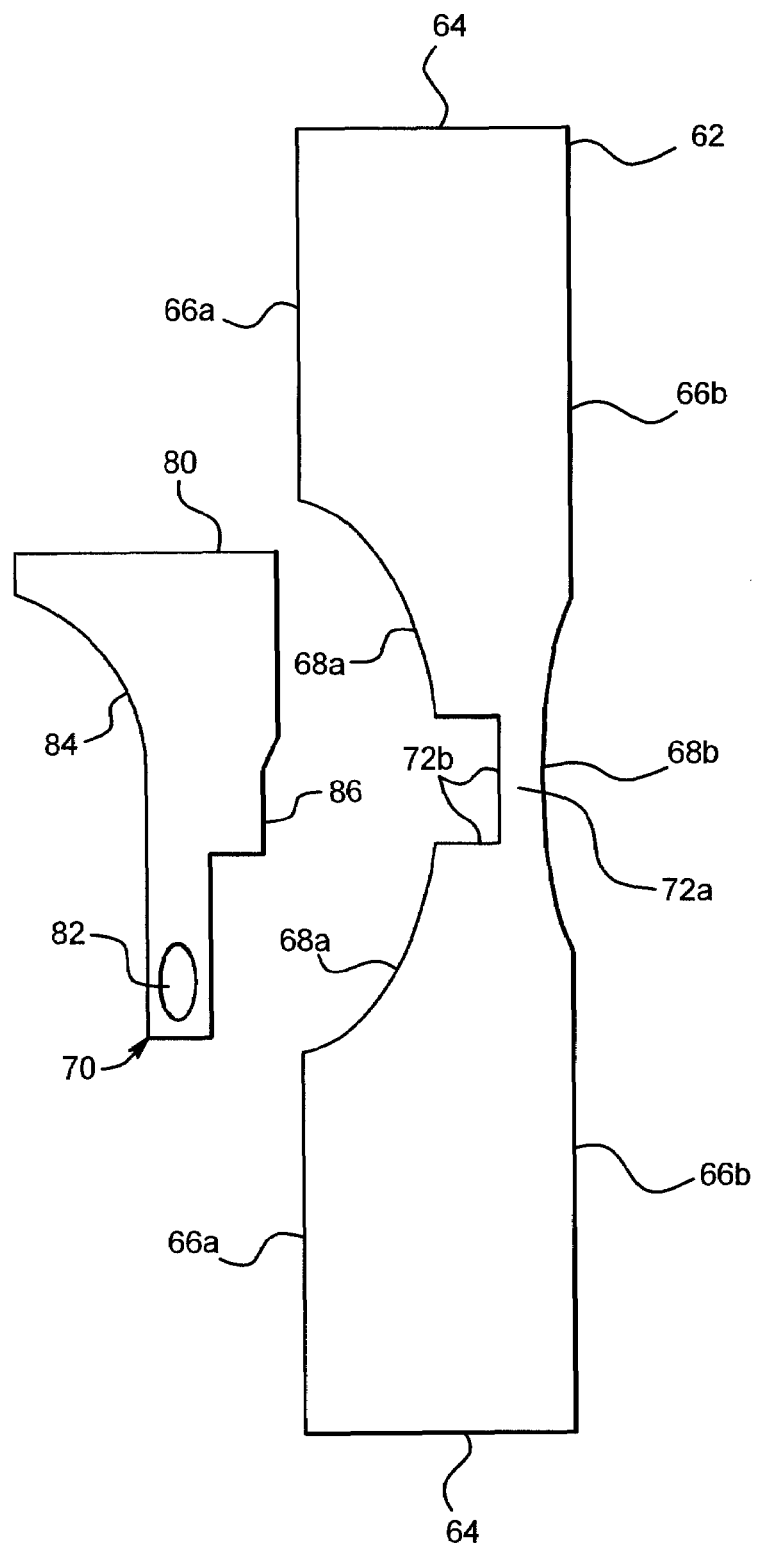
FIGS. 6 to 9 are elevation views illustrating another dual chamber bag and method of making same according to the present disclosure.
Figure 7:
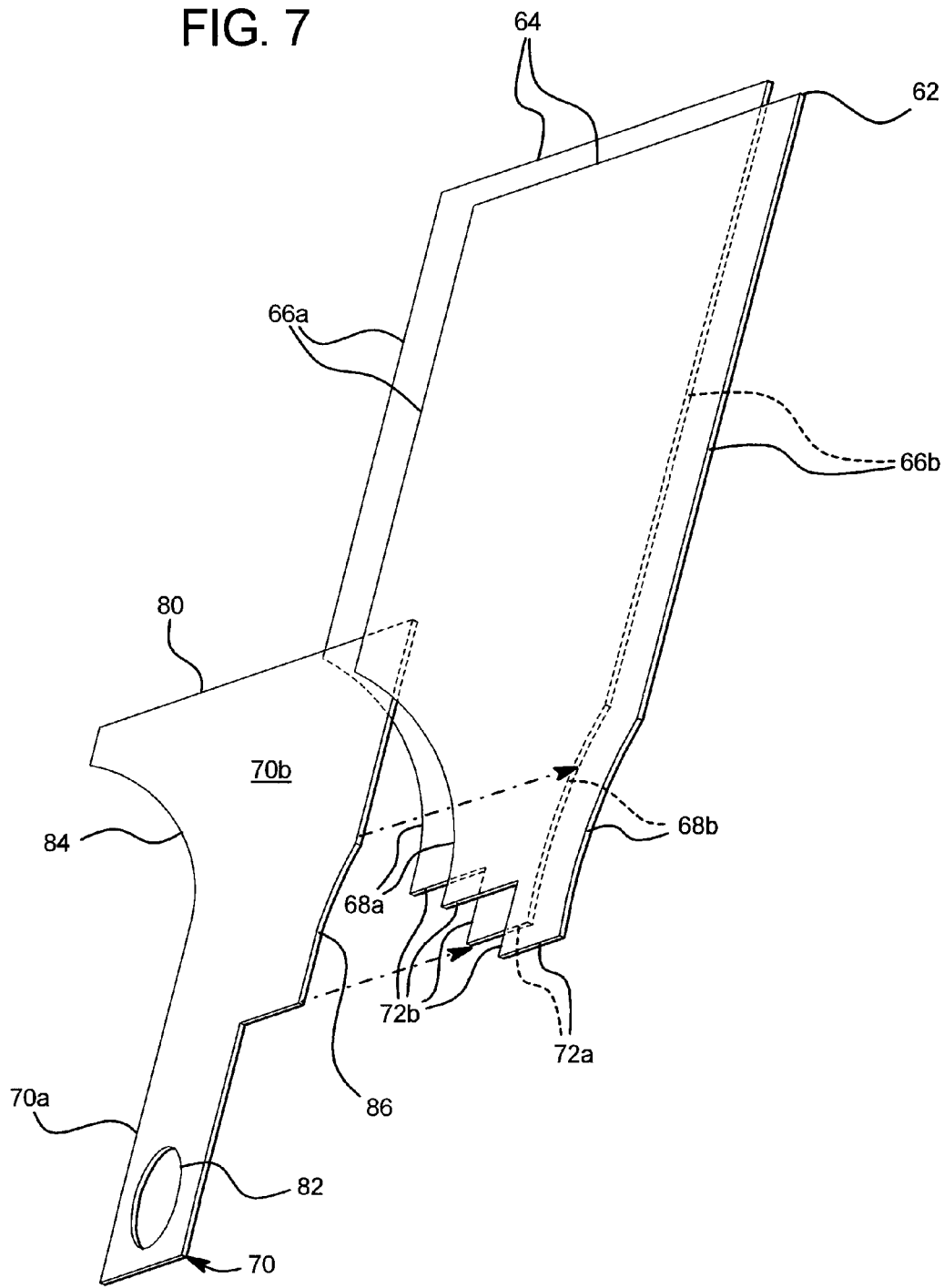
Figure 8:
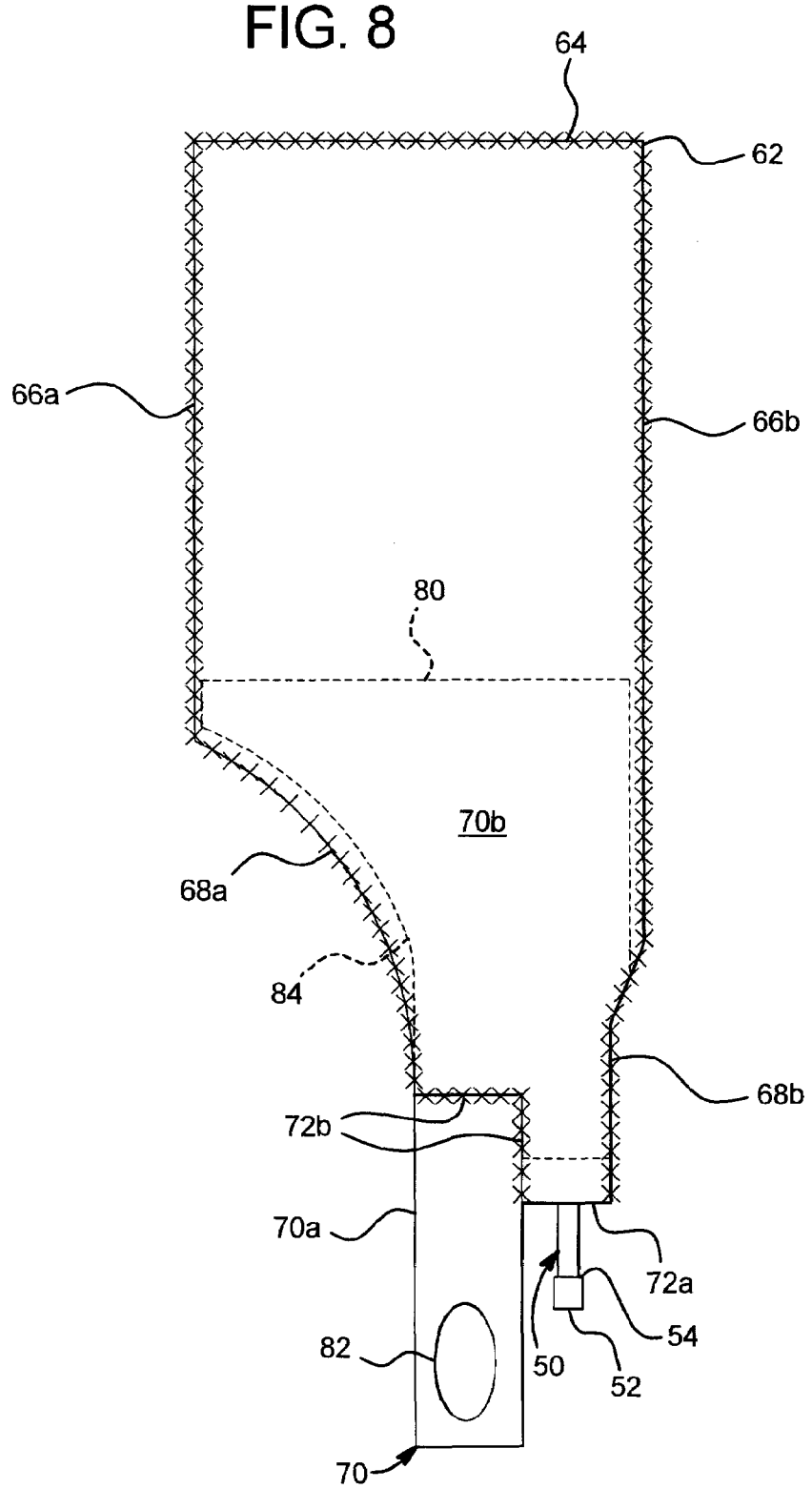
Figure 9:
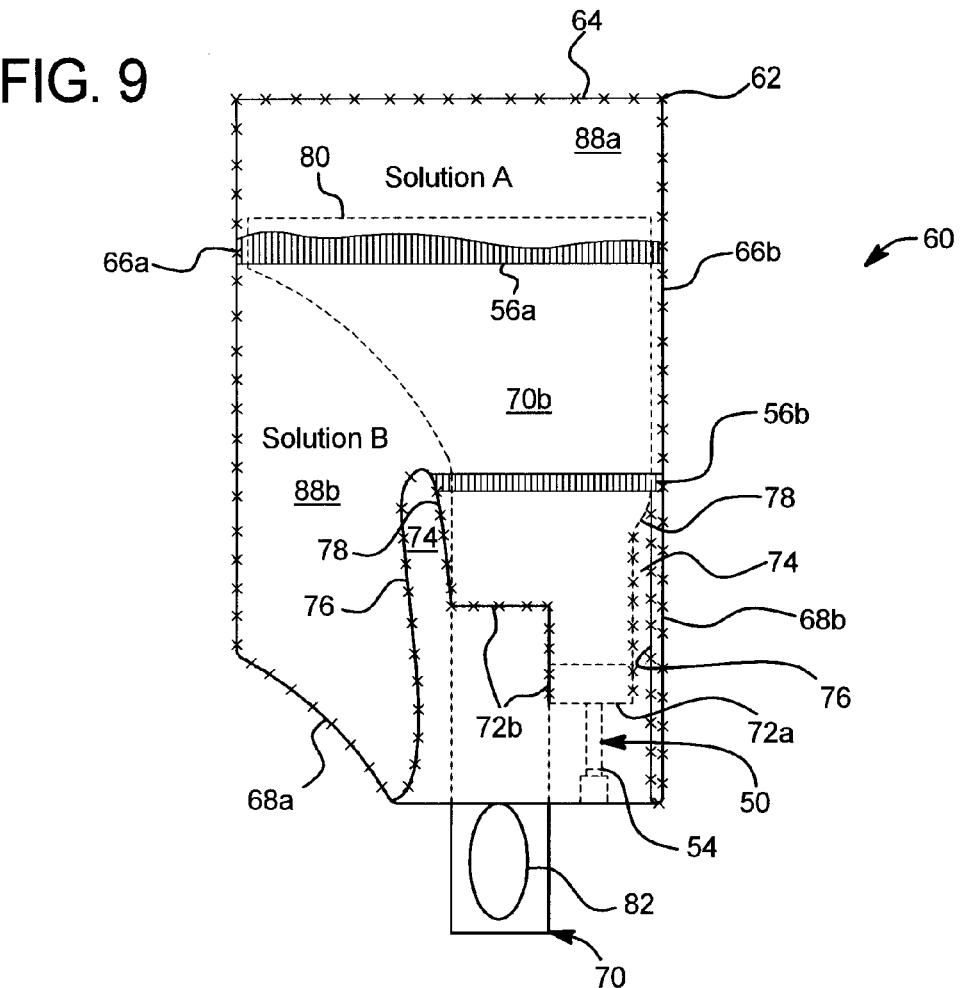
Figure 10:
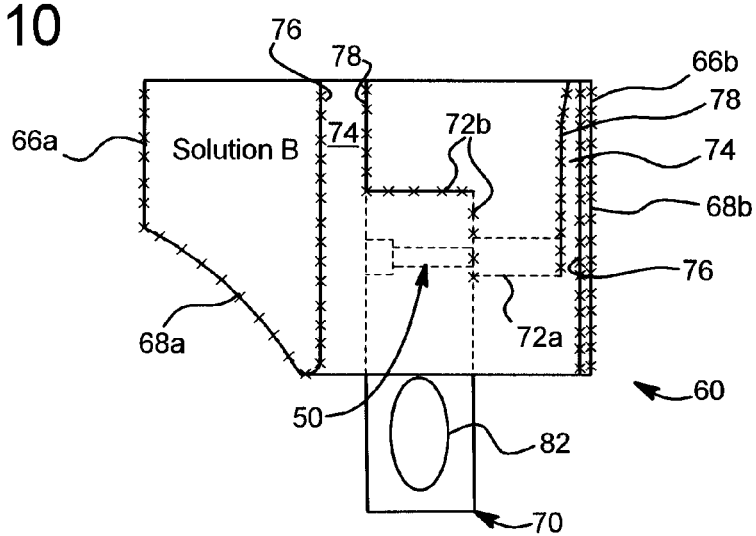
FIG. 10 is an elevation view of an alternative embodiment of the dual chamber bag of FIG. 9.

Referring now to FIGS. 6 to 9, a second primary embodiment of the dual chamber solution bag according to the present disclosure is illustrated by bag 60 (FIG. 9). FIGS. 6 to 8 show various stages of manufacturer of bag 60. FIG. 9 shows one embodiment for completed bag 60. FIG. 10 shows another embodiment for dual chamber bag 60.

One primary difference between bag 60 and bag 30 of FIGS. 5A and 5B is that the pull string of bag 30 is replaced by handle 70, which in the illustrated embodiment is a piece of plastic film or sheeting, such as the same sheeting used to form enclosure 62. Enclosure 62 also has a different shape than enclosure 32 of bag 30. Another primary difference for dual chamber bag 60 is that enclosure 62 is folded at the bottom of the bag, near handle 70, and is welded at opposing upper seam 64. As seen in FIGS. 6 to 9, sheet handle 70 includes an outer pull portion 70a, which resides outside chamber 62, and which defines an aperture 82 sized for example to accept a finger or fingers of the patient or caregiver. Handle 70 also expands in size at an inner portion 70b, which is maintained within enclosure 62. The larger portion 70b is sized to open all or most all of a frangible or peel seal when the patient or caregiver grasps and pulls handle 80.

FIG. 7 illustrates that enclosure 62 is formed by folding the enclosure at fold line 72a, such that upper seam 64, and side seams 66a, 66b, 68a and 68b can be welded via any of the embodiments discussed herein. Also, enclosure 62 is welded at seams 72b and 72c discussed in further detail below. FIG. 7 further illustrates how sheeting handle 70 is integrated into enclosure 62, namely, it is inserted near the bottom of enclosure 62, so that a curved edge 84 of handle 70 comes into substantial alignment with curved seam 68a of enclosure 62.

FIG. 8 illustrates a sealed enclosure 62 prior to the enclosure being folded into itself to protect against inadvertent breaking of seal 54 of access system 50. Here, handle 70 is sealed within enclosure 62, such that portion 70b resides within enclosure 72 and portion 70a remains outside of enclosure 72. Enclosure 62 is welded at seams 64, 66a, 66b, 68a, 68b and 72b. The upper end of enclosed portion 70b of handle 70 expands at an area where a first frangible or peel seal is made as seen in FIG. 9.

Seal 68b does not include the side of the portion 70b of handle 70. That is, sides of enclosure 62 are welded together to form 68b. Likewise, seal 68a does not include edge 84 of handle 70. Seal 72b however does include handle 70. In this manner, enclosure 62 at seal 72b moves with handle 70 as handle 70 is grasped and pulled, which in turn moves inner portion 70b of handle 70 relative to seals 68a and 68b.

FIG. 9 shows a completed dual chamber bag 60. Here, enclosure 62 is folded within itself to form inner opening 74, which includes a continuous opening around an inner opening wall 78 and outer opening wall 76 of enclosure 62. Enclosure 62 is folded into itself until access system 50 is hidden within enclosure 62.

First and second frangible seals 56a and 56b are then applied to enclosure 62. Frangible seal 56a seals sheets of enclosure 62 and an upper end 80 of handle 70. Upper end 80 spans substantially all of the width of enclosure 62, such that seal 56a opens a large area for solution A housed in first chamber 88a to mix properly and readily with solution B maintained within chamber 88b. As illustrated, frangible seal 56a separates chamber 88a from chamber 88b.

A second frangible seal 56b is provided to separate solution B of chamber 88b from an access area and from reaching access system 50. When the patient or caregiver pulls handle 70, e.g., via opening 82, inner portion 70b tears through frangible seals 56a and 56b virtually simultaneously, so that solutions A and B mix and also so that the mixed solution reaches seal 54 of access system 50 for the first time. Thus, even if the patient breaks access system seal 54 prior to opening peel seals 56a or 56b, no single solution can reach the patient. Alternatively, portion 70b is welded with seams 68a and 68b, and seal 56b is broken by applying pressure to the outside of enclosure 62 after frangible seal 56a is broken.

It is possible with bag 70 that frangible seal 56b could be broken before frangible seal 56a is broken, enabling only solution B to reach access assembly seal 54. If the patient or caregiver then breaks frangible seal 54, solution B alone could reach the patient. To remedy the above, FIG. 9 illustrates an alternative embodiment for dual chamber bag 60, in which access system 50 is rotated ninety degrees with respect to its position in bag 60 of FIG. 9. In dual chamber bag 60 of FIG. 10, access system 50 is very difficult to locate and open until handle 70 is pulled and both frangible seals 56a and 56b are broken. The configuration of access system 50 in FIG. 10 adds another layer of security and safety to dual chamber bag 60.

Figure 11A:
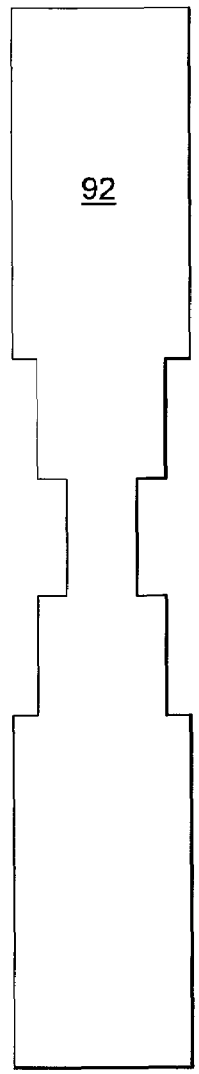
Figure 11B:
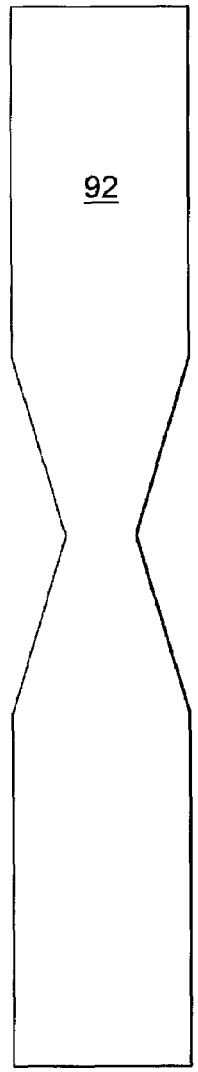
Figure 11C:
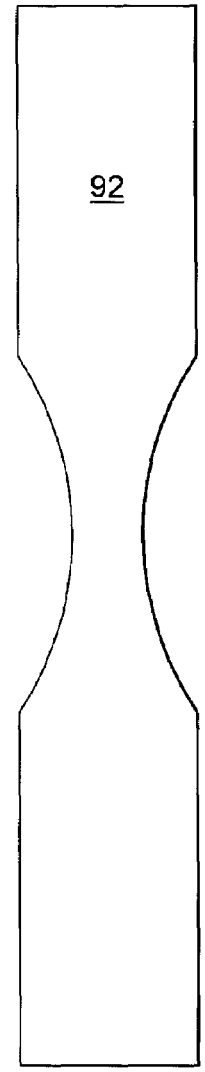
Figure 19A:
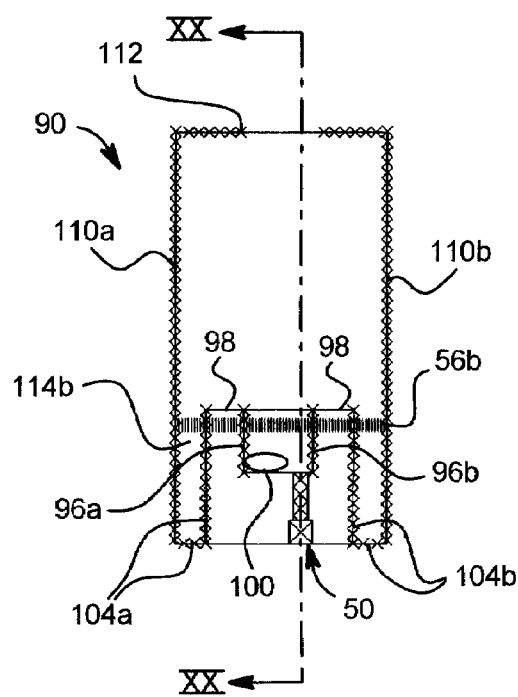
Figure 19B:
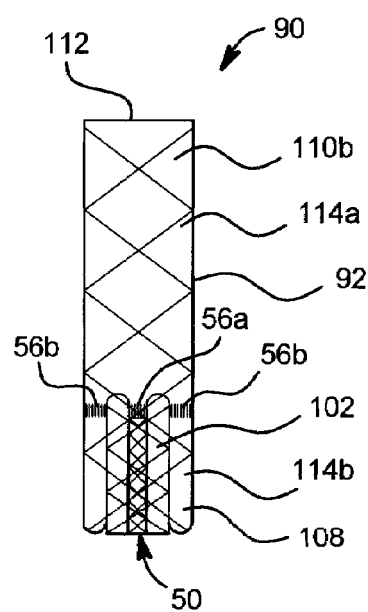
Figure 20B:
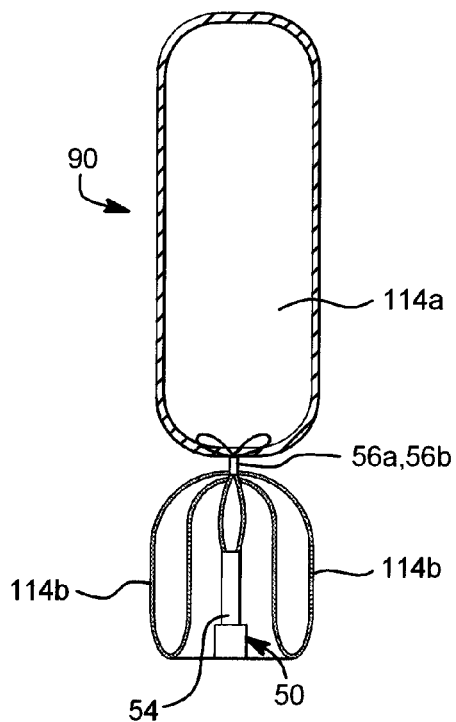
Figure 20A:
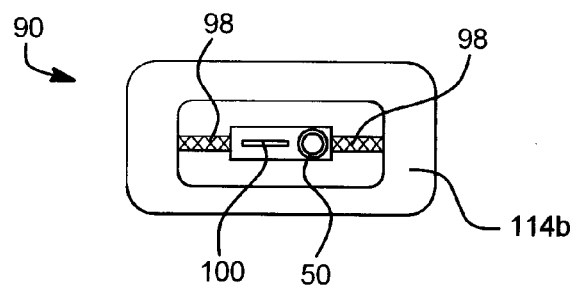

Referring now to FIGS. 11A to 11C, 12A, 12B, 13A, 13B, 14A, 14B, 15A, 15B, 16A, 16B, 17A, 17B, 18A, 18B, 19A, 19B and 20A to 20C a yet further alternative dual chamber bag of the present disclosure and method of making same is illustrated by bag 90 (FIGS. 20A to 20C). FIGS. 11A to 11C show three different configurations for enclosure 92 of dual chamber bag 90. FIG. 11A illustrates an enclosure 92 having a stepped shaped bottom. FIG. 11B illustrates enclosure 92 having a triangular shaped bottom. FIG. 11C illustrates enclosure 92 having a rounded bottom. For purposes of illustration, the stepped shaped bottom of FIG. 11A is shown in the remaining figures. It should be appreciated however that the teachings shown in the remaining figures are applicable to any of the configurations of enclosure 92 of FIGS. 11A to 11C and to other suitable shapes that may be readily formed by those of skill in the art.

Figure 12A:
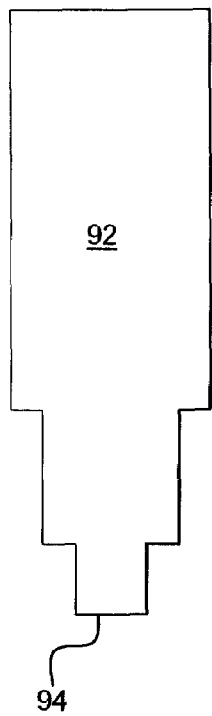
Figure 12B:
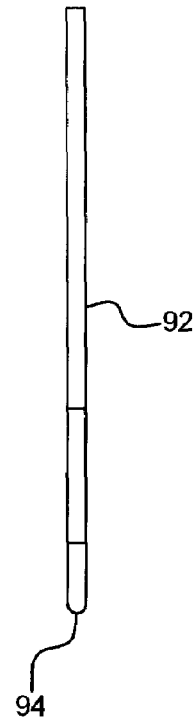
Figure 13A:
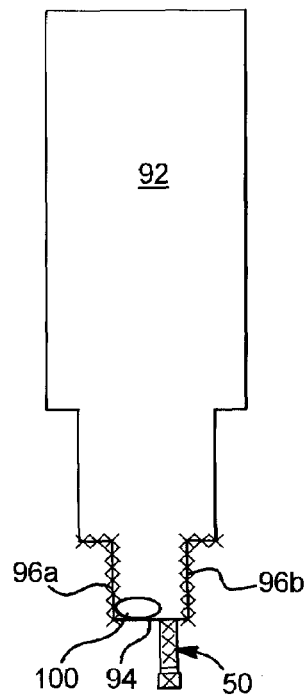
Figure 13B:
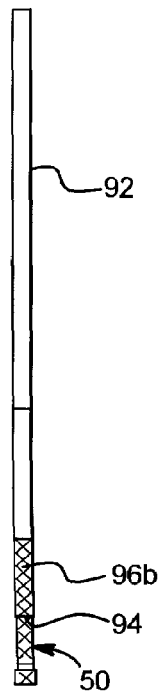

FIGS. 12A and 12B show that the first step in the manufacturer of dual chamber bag 90 is to fold enclosure 92 at fold line 94. FIGS. 13A and 13B illustrate that the next step includes the formation of welded seams 96a and 96b along a portion of the sides of enclosure 92. Also, access system 50 is welded to enclosure 92 at fold line 94. Further, a handle 100, such as a loop or tab, is welded to the outside of enclosure 92.

Figure 14A:
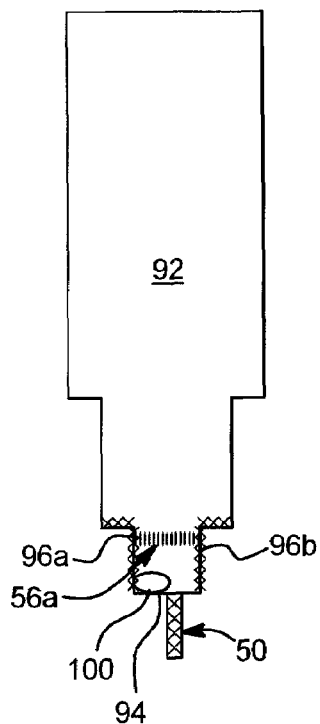
Figure 14B:
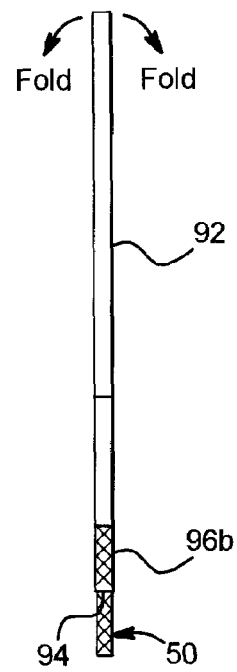
Figure 15A:
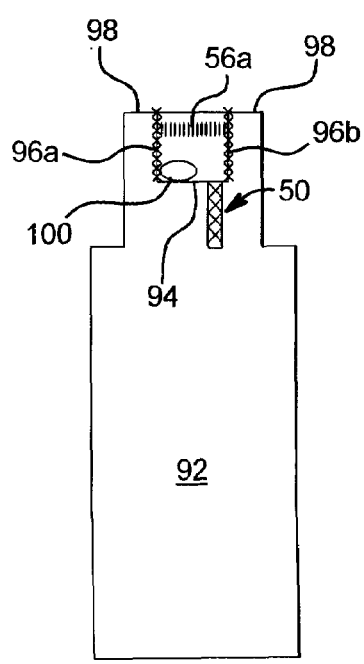
Figure 15B:
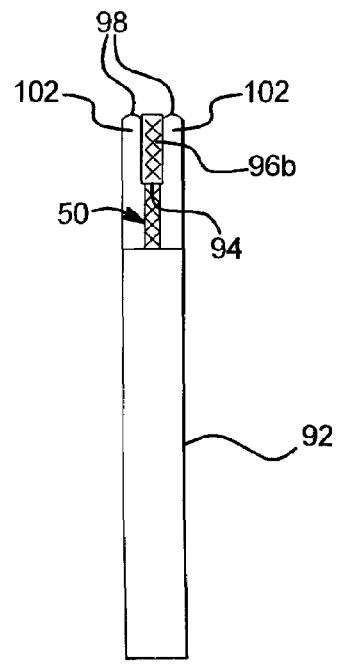

FIGS. 14A and 14B illustrate the addition of the first frangible seal 56a, which separates access system 50 from the remainder of enclosure 92. Air is maintained between frangible seal 56a and access system 50. FIGS. 15A and 15B illustrate a second folding operation resulting in second fold lines 98 and the creation of channel 102 between the access system 50 and handle 100 area and the outer sheets of enclosure 92.

Referring now to FIGS. 16A and 16B, another step in the manufacturer of dual chamber bag 90 is the addition of welded seams 104a and 104b, which further enclose chamber 102. FIG. 16B shows how weld 104b is made around inner weld 96b. FIGS. 17A and 17B illustrate a third folding operation, in which fold lines 106 are created by folding enclosure 92 at a portion of weld seams 104a and 104b. The additional fold creates an outer chamber 108, which surrounds inner chamber 102.

Figure 18A:
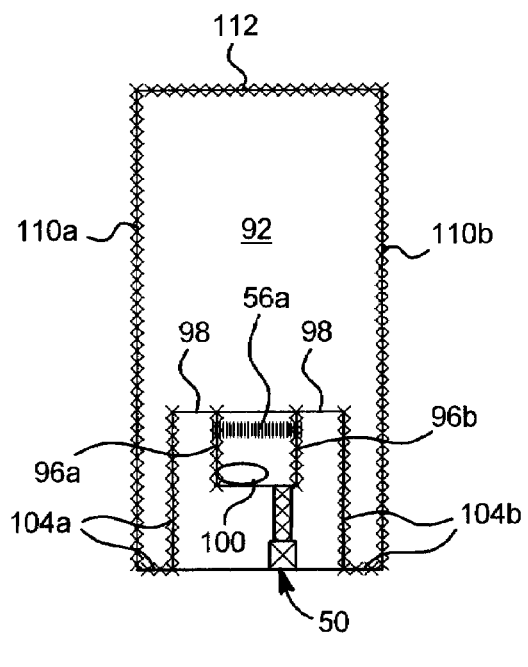
Figure 18B:
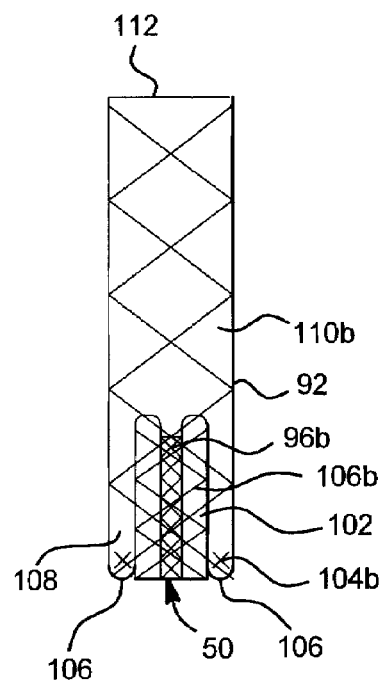

FIGS. 18A and 18B illustrate the addition of outer welds 110a, 110b and 112. Outer welds seal outer chamber 108 completely. FIGS. 19A and 19B illustrate the addition of the second peel seal or frangible seal 56b. The second frangible seal 56b is made to divide outer chamber 108 into first fluid holding chamber 114a and second fluid holding chamber 114b as seen best in FIG. 19B. Frangible seal 56a seals access system 50 from chamber 114a as seen in FIG. 19B.

FIGS. 20B and 20C illustrate dual chamber bag 90 in further detail. FIG. 20B is a section view of FIG. 19A taken along line XX-XX shown in FIG. 19A. FIG. 20B shows the general shape of first chamber 114a and second chamber 114b. It also shows that frangible seals 56a and 56b are aligned and overlapping. Second chamber 114b is an annular or continuous chamber in which a second solution is trapped between outer and inner cylindrical or continuous walls. Second chamber 114b surrounds an empty space in which access system 50 and handle 100 are located.

When the user pulls handle 100, peel seal 56b between chambers 114a and 114b is subjected to a force almost perpendicular to the walls of container 90, due to the folding of film of enclosure 92. In contrast, frangible seal 56a in the inner layers does not experience any stress during this action since the two inner most layers move together in the same direction. As a consequence of this difference in the direction of forces, frangible seal 56a separating chambers 114a and 114b breaks before inner frangible seal 56a, guaranteeing that mixing takes place before any liquid can reach seal 54 of access system 50. In the illustrated embodiment, frangible seal 56b is broken by applying pressure to the mixed open chambers, such that the increased pressure of the liquid causes frangible seal 56a to open and fluid to flow to access system 50.

Figure 21:
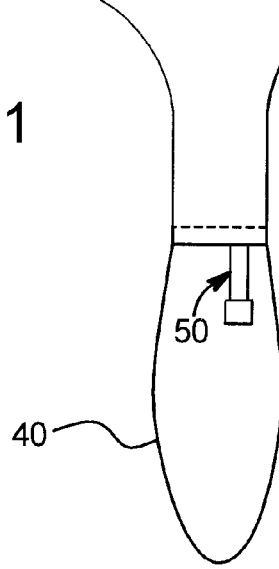
FIGS. 21 to 23 illustrate yet another alternative dual chamber bag and method of making same according to the present disclosure.
Figure 22:
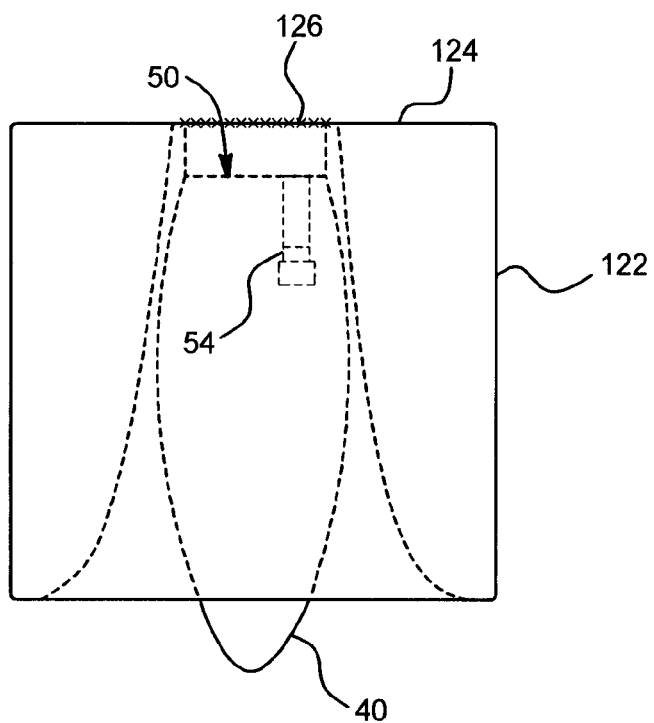
Figure 23:
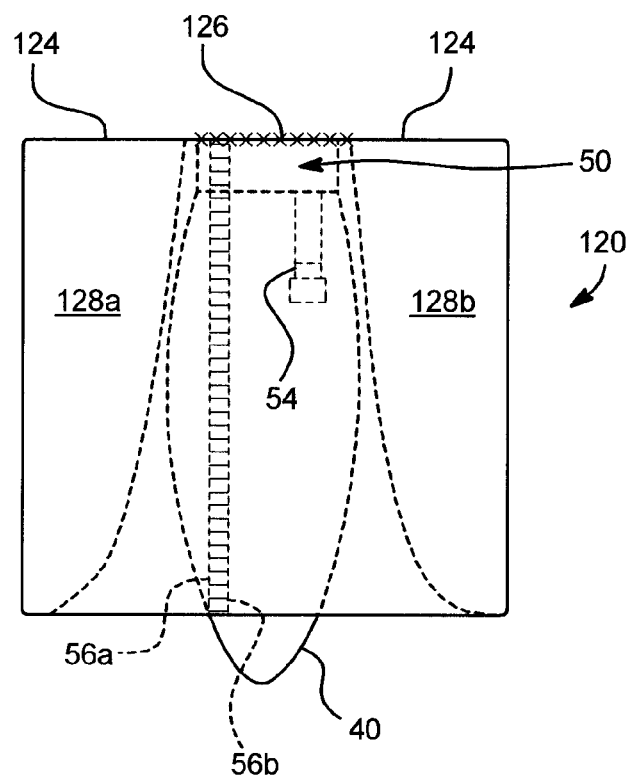

FIGS. 21 to 23 illustrate still a further alternative dual chamber bag 120 and method of making same, which includes the provision of a vertical frangible seal after access system 50 is pushed as far as it can go into enclosure 122. FIG. 22 shows that enclosure 122 at access system 50 is pushed into itself until that portion meets upper distal wall 124 of enclosure 122. String 40 in enclosure 120 is maintained wholly outside of enclosure 122 and indeed can be welded to the outside of enclosure 122. Access system 50 is welded at seam 126 to upper edge 124 of enclosure 122.

FIG. 23 illustrates that upper and lower frangible seals 56a and 56b (located one on top of the other) separate and form first and second chambers 128a and 128b. When the user pulls cord 40, access system 50 is pulled through both upper and lower frangible seals 56a and 56b, allowing first and second fluids in first and second chambers 128a and 128b, respectively, to mix. It should be appreciated that even if the user some how punctures seal 54 of access system 50 prior to pulling access system 50 through first and second frangible seals 56a and 56b, weld 126 seals first and second chambers 128a and 128b from access system 50, such that no fluid can be transferred to the patient.

Figure 24:
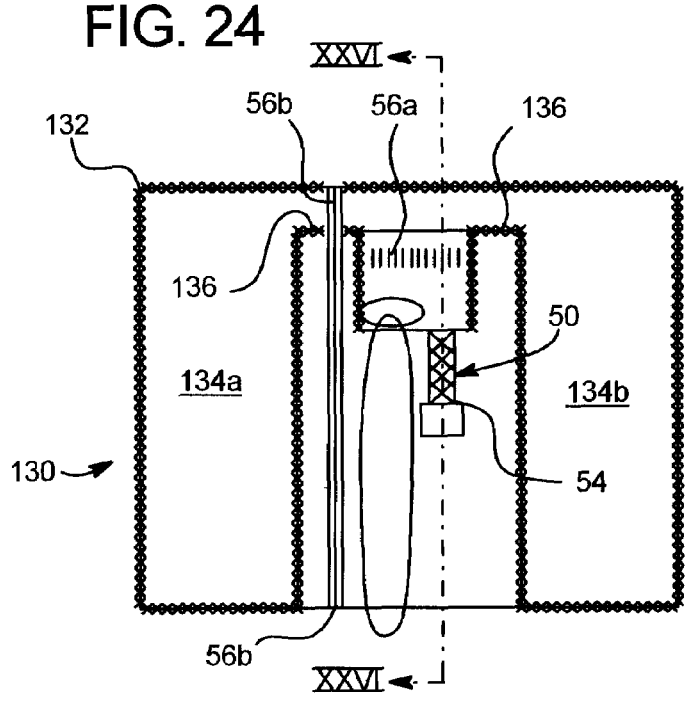
FIGS. 24 to 26 illustrate still another alternative dual chamber bag and method of making same according to the present disclosure.
Figure 25:
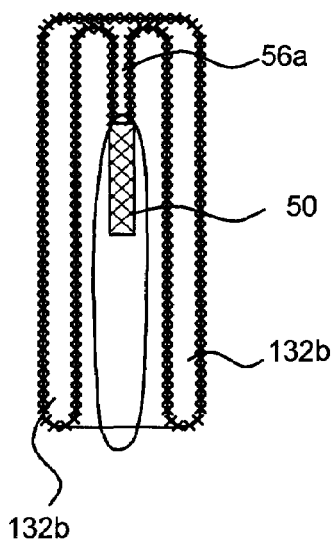
Figure 26:
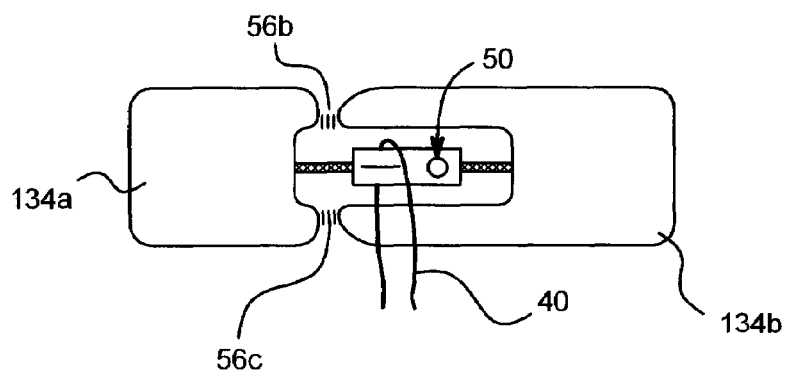

FIGS. 24 to 26 illustrate another vertical frangible seal embodiment. This embodiment includes three frangible seals 56a, 56b and 56c. Dual chamber container 130 includes an enclosure 132 formed in much the same way as is enclosure 92 of container 90 discussed above. Here, first seal 56a forms a safety seal between enclosure 132 and access system 50. Thus even if the patient or user breaks seal 54 of access system 50 prior to vertical frangible seals 56b and 56c being broken, frangible seal 56a isolates access system 50 from enclosure 132. Vertical peel seals 56b and 56c as seen in FIGS. 24 and 26 separate enclosure 132 into first and second fluid carrying chambers 134a and 134b. The user pulls handle or cord 40, which is completely external to chamber 132 to rip an upper inner edge 136 of enclosure 132 through frangible seals 56b and 56c, allowing fluid from first and second chambers 134a and 134b to mix.

It should be appreciated that many of the dual chamber containers described herein, such as container 130 can be opened readily for example by hanging cord 40 around a door handle and allowing enclosure 132, holding first and second fluids to drop hangman style to automatically mix the first and second fluids. Here, access system 50 points vertically upward (imagine container 130 in FIG. 25 turned upside down), such that the weight of fluid will not place any pressure on safety frangible seal 56a. The user can then squeeze dual chamber container 130 to pop or open frangible seal 56a.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A multiple chamber medical fluid bag comprising:
   a flexible enclosure;
   a first fluid chamber formed in the enclosure;
   a second fluid chamber formed in the enclosure;
   a divider embedded into the enclosure, the divider including a handle;
   a frangible seal separating the first and second fluid chambers; and
   an access port connected to the enclosure, the frangible seal communicating with the divider such that the handle of the divider can be moved to break the frangible seal and to expose the access port.

2. The multiple chamber medical fluid bag of claim 1, wherein the enclosure is folded so as to cover the access port before the frangible seal is broken.

3. The multiple chamber medical fluid bag of claim 1, wherein the frangible seal is a first frangible seal, and which includes a second frangible seal isolating the first and second fluid chambers from the access port.

4. The multiple chamber medical fluid bag of claim 3, wherein the divider is further configured to break the second frangible seal.

5. The multiple chamber medical fluid bag of claim 1, wherein the divider includes at least one characteristic selected from the group consisting of: being plastic, being a film, being flexible and being semi-rigid.

6. A multiple chamber medical fluid bag comprising:
   a flexible enclosure;
   a first fluid chamber formed in the enclosure;
   a second fluid chamber formed in the enclosure;
   an access port connected to the enclosure;
   a first frangible seal separating the access port from the first and second fluid chambers;
   a second frangible seal separating the first and second fluid chamber and configured to rupture before the first frangible seal ruptures; and
   a handle operable with the access port, the handle and access port separated from the first and second fluid chambers by the first frangible seal.

7. The multiple chamber medical fluid bag of claim 6, wherein the enclosure is folded so as to cover the access port before the frangible seal is broken.

8. The multiple chamber medical fluid bag of claim 7, wherein the enclosure is folded multiple times.

9. The multiple chamber medical fluid bag of claim 6, wherein the first frangible seal is positioned beneath the second frangible seal.

10. The multiple chamber medical fluid bag of claim 6, which includes at least one weld forming at least one seam of the enclosure together.

* * * * *

UNITED STATES PATENT AND TRADEMARK OFFICE
CERTIFICATE OF CORRECTION

PATENT NO. : 7,618,406 B2 Page 1 of 1
APPLICATION NO. : 11/625683
DATED : November 17, 2009
INVENTOR(S) : Rodolfo Roger It is certified that error appears in the above-identified patent and that said Letters Patent is hereby corrected as shown below:

On the title page, item [56]:

In References Cited, the fourteenth reference listed, change "3/2000" to --1/2000--.

In Column 5, Line 61, change "to 20C" to --and 20B--.

In Column 5, Line 63, change "to 20C" to --and 20B--.

In Column 6, Line 40, change "FIG. 20B and 20C" to --FIG. 20B--.

Signed and Sealed this

Thirtieth Day of March, 2010

David J. Kappos
*Director of the United States Patent and Trademark Office*